(12) United States Patent
Turos et al.

(10) Patent No.: US 8,110,678 B2
(45) Date of Patent: Feb. 7, 2012

(54) ANTIBIOTIC-BOUND POLY(CAPROLACTONE) POLYMER

(75) Inventors: Edward Turos, Wesley Chapel, FL (US); Michelle Leslie, Tampa, FL (US)

(73) Assignee: University of South Florida, Tampa, FL (US)

( * ) Notice: Subject to any disclaimer, the term of this patent is extended or adjusted under 35 U.S.C. 154(b) by 25 days.

(21) Appl. No.: 11/746,704

(22) Filed: May 10, 2007

(65) Prior Publication Data

US 2007/0265243 A1 Nov. 15, 2007

Related U.S. Application Data

(60) Provisional application No. 60/747,061, filed on May 11, 2006.

(51) Int. Cl.
*C07D 205/08* (2006.01)
*C07D 405/12* (2006.01)
*C07D 313/04* (2006.01)

(52) U.S. Cl. ........ 540/355; 549/266; 549/271; 549/342; 528/354

(58) Field of Classification Search .................. 540/355; 549/266, 271
See application file for complete search history.

(56) References Cited

U.S. PATENT DOCUMENTS

| | | | |
|---|---|---|---|
| 5,025,025 A * | 6/1991 | Bhagwat et al. | 514/340 |
| 5,629,381 A * | 5/1997 | Isozaki | 525/131 |
| 5,917,067 A * | 6/1999 | Cotarca et al. | 549/266 |
| 6,967,208 B2 | 11/2005 | Pinto et al. | |
| 7,091,219 B2 | 8/2006 | Freskos et al. | |

OTHER PUBLICATIONS

Woster, Journal of Medicinal Chemistry (1989), 32(6), 1300-7.*
Adger et al., J. Chem. Soc., Chem. Commun., 1995, 1563-1564.*
Turos, E., J. Shim, Y. Wang, K. Greenhalgh, G. Reddy, S. Dickey, and D. Lim. 2005. N-Methylthio B-Lactam Antibacterials: Effects of the C3/C4 Ring Substituents on Anti-MRSA Activity. Bioorganic & Medicinal Chemistry vol. 13. p. 6289-6308.
Turos, E., J. Shim, Y. Wang, K. Greenhalgh, G. Reddy, S. Dickey, and D. Lim. 2007. Antibiotic-Conjugated Polyacrylate Nanoparticles: New Opportunities for Development of Anti-MRSA Agents. Bioorganic and Medicinal Chemistry Letters. vol. 17 pp. 53-56.
Sinha, V.R., K. Bansal, R. Kaushik, R. Kumria, and A. Trehan. 2004. Poly-e-Caprolactone Microsphers and Nanospheres: an Overview. International Journal of Pharmaceutics vol. 278, pp. 1-23.
"Hydrophilic Aliphatic Polyesters: Design, Synthesis, and Ring-Opening Polymerization of Functional Cyclic Esters" Marcomolecules, 2000, 33,4619-4627.

* cited by examiner

*Primary Examiner* — Mark Berch
(74) *Attorney, Agent, or Firm* — Wanhua Zhao; Smith & Hopen, P.A.

(57) ABSTRACT

This invention is the design and synthesis of a caprolactone monomer which bears a pendant protected carboxyl group. This monomer has been copolymerized with caprolactone in varying ratios. After polymerization, the protecting group can be removed and an antibiotic can be attached as a new pendant group. The bioactivity of the antibiotic-bound poly(caprolactone) polymer is described.

6 Claims, 5 Drawing Sheets

PRIOR ART

Reagents and conditions: (a) PPh$_3$, C$_6$H$_6$, 12h, rt; (b) 20% NaOH$_{(aq)}$, 5h, rt.

| Drug mass | ZOI |
|---|---|
| 20 ug | 11mm |
| 50 ug | 20mm |
| 100 ug | 20mm |

ANTIBIOTIC-BOUND POLY(CAPROLACTONE) POLYMER

CROSS-REFERENCE TO RELATED APPLICATIONS

This application claims priority from U.S. Provisional Application No. 60/747,061 filed on May 11, 2006, entitled "Antibiotic-Bound Poly(Caprolactone) Polymer".

STATEMENT OF GOVERNMENT INTEREST

This invention was made with Government support under Grant No. RO1 A1 51351 awarded by the National Institutes of Health. The Government has certain rights in the invention.

FIELD OF INVENTION

This invention relates to attaching one or more bioactive molecules to the same polymer, and also for attachment before or after polymerization

BACKGROUND OF THE INVENTION

The delivery of water-insoluble drugs to targets within the human body is a challenge that presently places strict limitations on what drugs can be applied clinically. The need for methods which overcome this is of high priority in the development of new therapeutics for treatment of human disease.

The development of antibiotics for control of pathogenic bacteria has been of pressing need in this era of drugresistant infections. N-Methylthiolated b-lactams have been identified as a new family of antibacterial agents active against *Staphylococcus* bacteria, including methicillin-resistant *Staphylococcus aureus* (MRSA). (See Turos, E.; Konaklieva, M. I.; Ren, R. X. F.; Shi, H.; Gonzalez, J.; Dickey, S.; Lim, D. *Tetrahedron* 2000, 56, 5571; Bart Heldreth, Timothy E. Long, Seyoung Jang, Suresh K. R. Guntireddygari, Edward Turos, Sonja Dickey, Daniel V. Lim, "N-Thiolated b-Lactam Antibacterials: Effects of the N-Organothio Substituent on anti-MRSA Activity," *Bioorganic and Medicinal Chemistry* 14, 3775-3784 (2006); and Edward Turos, Jeung-Yeop Shim, Yang Wang, Kerriann Greenhalgh, G. Suresh Kumar Reddy, Sonja Dickey, Daniel V. Lim, "Antibiotic-Conjugated Polyacrylate Nanoparticles: New Opportunities for Development of Anti-MRSA Agents," *Bioorganic and Medicinal Chemistry Letters* 16, in press (2006); which are incorporated herein by reference).

The compounds have also displayed promising anticancer properties. These lactams exert their growth inhibitory effects on bacteria through a mode of action that is distinctively different to that of other b-lactam antibiotics, and possess structure-activity patterns unlike those already mapped for other b-lactam antibacterials such as the penicillins. One of the major limitations in the potential application of these N-thiolated b-lactam compounds, however, is their exceedingly low water solubility.

Drug delivery vehicles such as liposomes and gold nanoparticles have been developed to improve bioavailability, efficacy, and specificity of pharmaceutical compounds, particularly for anticancer agents, but nanoparticles have received surprisingly little attention in the antibiotic and infectious disease area. Some of the few notable examples have included antibiotic-encapsulated polymeric nanoparticles and liposomes, biodegradable nanospheres and surface-coated gold and silver nanoparticles.

SUMMARY OF INVENTION

In one embodiment, the invention provides an effective drug delivery platform that would enhance the water solubility of the lactams, without sacrificing inherent bioactivity.

In another embodiment, the invention provides for the development of antibacterial polyacrylate nanoparticles based on well-precedented emulsion polymerization procedures.

This invention addresses this need, and demonstrates the use of antibiotic-bound poly(caprolactone) polymers as anti-infective materials for biomedical applications in the prevention of bacterial infections.

In a first embodiment, the invention includes a functionalized compound comprising at least one caprolactone ring with an appended functional group. A plurality of methylene groups act as a spacer between the lactone ring and the functional group. In a preferred embodiment, the functional group is an antibiotic, such as a N-thiolated β-lactam. The functional group is preferably covalently bonded.

In an alternate embodiment, a method is provided for producing the functionalized compound of the previous embodiment. The method includes providing a at least one caprolactone ring with a protecting group spaced apart from the caprolactone ring by a plurality of methylene groups. The protecting group is then cleaved from the caprolactone ring and replaced by bonding a functional group to the caprolactone ring. Illustrative reagents for cleaving the protecting group include 10% pd/C as a catalyst in the presence of $H_{2(g)}$ and ethyl acetate (EtOAc). The protecting group is selected from the group consisting of alcohol protecting groups, amine protecting groups, carbonyl protecting groups and carboxyl protecting groups. In a preferred embodiment, the protecting group is selected from the group consisting of a benzel ester and a tert-butyl ester. As with the previous embodiment, the functional group is an antibiotic such as a N-thiolated β-lactam.

In another embodiment, the invention includes the compound represented by the formula:

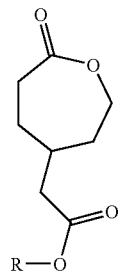

or a pharmaceutically acceptable salt or ester thereof, wherein is selected from the group consisting of water-insoluble drugs, antibiotics, lactams, β-lactams, N-thiolated β-lactams and protecting groups. The protecting group is selected from the group consisting of alcohol protecting groups, amine protecting groups, carbonyl protecting groups and carboxyl protecting groups.

In yet another embodiment, the invention includes the compound represented by the formula:

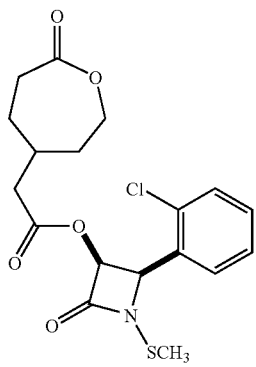

or a pharmaceutically acceptable salt or ester thereof.

In another embodiment, the invention includes the compound represented by the formula:

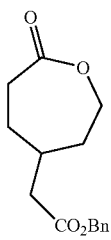

or a pharmaceutically acceptable salt or ester thereof.

In still another embodiment, the invention includes the compound represented by the formula:

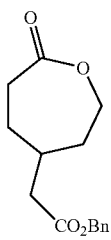

or a pharmaceutically acceptable salt or ester thereof.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

N-thiolated β-lactams

New family of anti-MRSA and anti-Bacillus agents that have recently been reported by our laboratory. Extensive SAR studies have shown that changing the N-thioalkyl substituent has a large effect on the bioactivity and that changes at the other positions of the ring exert a more subtle effect. Recent research in our group has been focused on covalent attachment of these and other antibiotics to polymers for drug delivery and for new biomaterials.

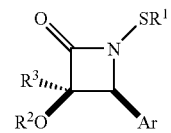

As used herein, the term "drug" to any therapeutic or prophylactic agent other than food which is used in the prevention, diagnosis, alleviation, treatment, or cure of disease in man or animal.

As used herein, the term "antibiotic" refers to any natural, synthetic, and semi-synthetic compound that has been identified as possessing antibacterial, antifungal, antiviral, or antiparasitic activity.

Polycaprolactones

Figure 1:
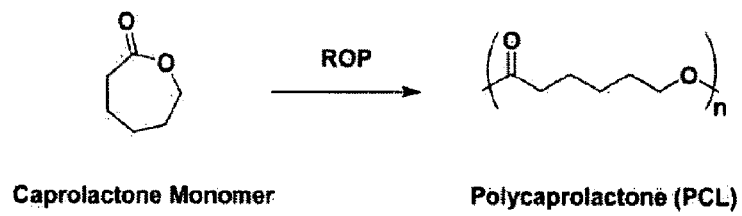
FIG. 1 shows the polymerization of a caprolactone monomer to polycaprolactone (PCL).

Polycaprolactone (PCL) is a biodegradable polyester which can be prepared by ring opening polymerization of ε-caprolactone using a catalyst such as stannous octanoate, as shown in FIG. 1. PCL is degraded by hydrolysis of its ester linkages in physiological conditions (such as in the human body) and is therefore useful as a biomaterial. PCL has been approved by the Food and Drug Administration (FDA) for use in the human body as (for example) a suture (sold under the brand name Monocryl™ or generically). In particular, PCL has been used in long term implantable devices, owing to its degradation which is relatively slow. (See V. R. Sinha, K. Bansal, R. Kaushik, R. Kumria and A. Trehan; Poly-ε-caprolactone microspheres and nanospheres: an overview, *International Journal of Pharmaceutics*, Volume 278, Issue 1, 18 Jun. 2004, Pages 1-23; which is incorporated herein by reference.)

Figure 2:
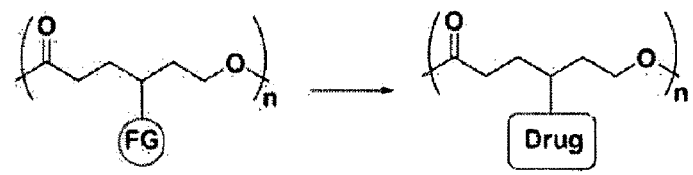
FIG. 2 shows the functionalized caprolactone polymer can be used for covalent binding of drug molecules.

The characteristics of PCL make is useful as a delivery mechanism for antibiotics. For example PCL is biodegradable (bulk hydrolysis of ester bonds), the byproducts of degradation are non-toxic (biocompatible), it is FDA approved and displays high permeability to many drugs. Therefore, the invention provides a functionalized caprolactone polymer can be used for covalent binding of drug molecules (FIG. 2).

Figure 3:
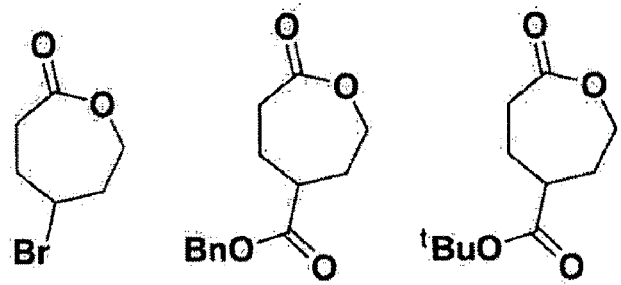
FIG. 3 shows examples of functionalized caprolactones from the literature.
Figure 4:
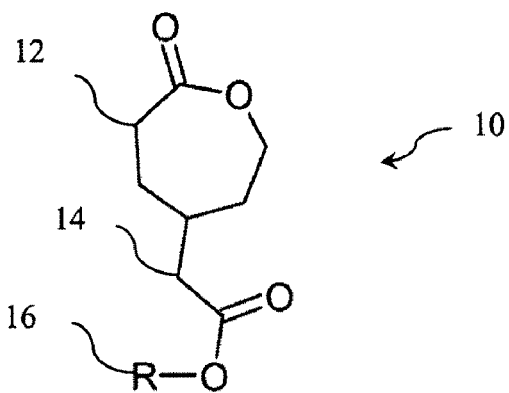
FIG. 4 shows the functionalized lactone of present invention.

The functionalized caprolactones of the prior art (Detrembleur et al Macromolecules, 2000, 33, 14-18 and Trollsas et at Macromolecules, 2000, 33, 4619-4627) are shown in FIG. 3. In contrast, the functionalized lactone 10 of present invention is shown in FIG. 4. Lactone 10 comprises at least one lactone ring 12, functional group 16 and at least one spacer 14. As it can be seen, functional group 16 is placed away from site of polymerization. Moreover, an additional methylene spacer 14 between functional group 16 and lactone ring 12 enhances further functionalization.

Figure 5A:
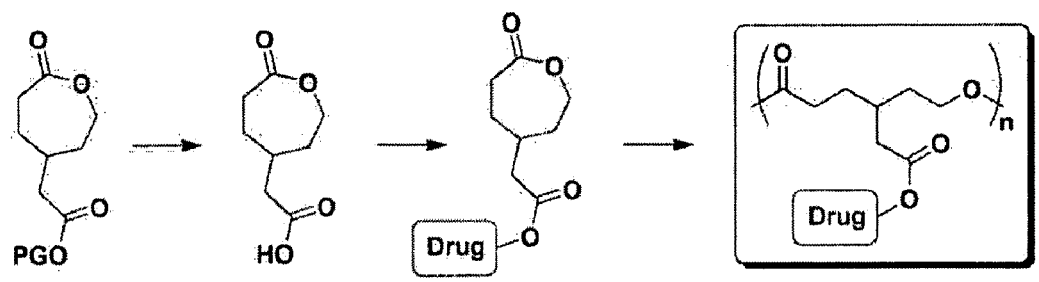
FIG. 5A shows drug appendage before polymerization.
Figure 5B:
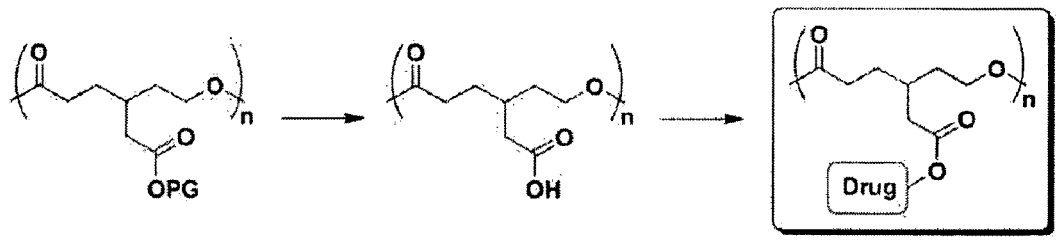
FIG. 5B shows drug appendage after polymerization.
Figure 6:
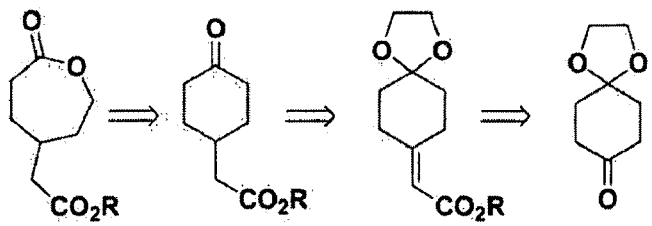
FIG. 6 shows lactone resynthesis.
Figure 7:
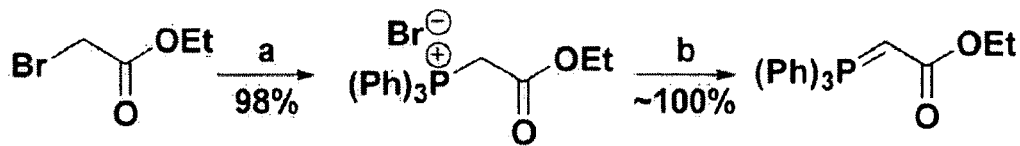
FIG. 7 shows ylide synthesis.

In another embodiment, the invention provides a method of producing an antibiotic-conjugated functionalized caprolactone (FIG. 5A and FIG. 5B). In Step 1 includes providing a caprolactone comprising lactone ring 12, methylene spacer 14 and protecting group 18. In Step 2, protecting group 18 is cleaved, preferably under mild conditions. Finally, in Step 3, drug of interest 20 is covalently bonded to the finished compound. FIG. 5A illustrates the method of appending a drug of interest to the functionalized lactone before polymerization. FIG. 5B illustrates the method of appending a drug of interest to the functionalized lactone after polymerization. Lactone retrosynthesis is shown in FIG. 6 and Ylide synthesis is shown in FIG. 7.

Example 1

The following represents an embodiment of the invention wherein 1,4-dioxaspiro[4.5]decan-8-one is used to synthesize a functionalized lactone bearing a pendent benzyl ester as the protecting group.

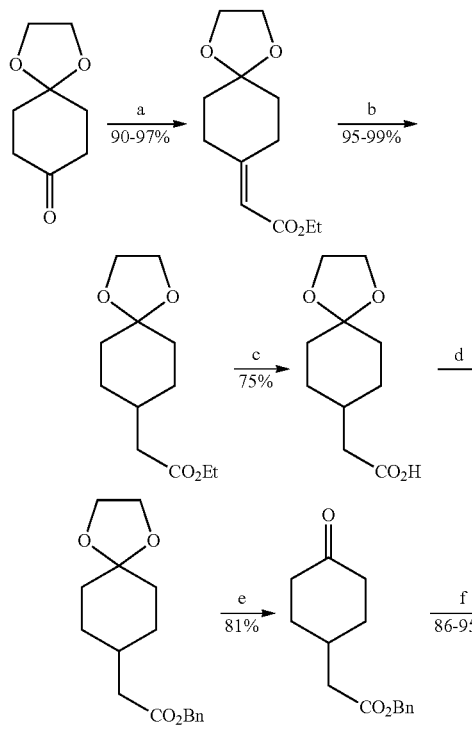

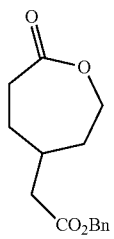

Reagents and conditions: (a) 2 eq. ylide, C$_6$H$_6$, 12 h, reflux; (b) 60 psi H$_{2(g)}$, cat. 10% Pd/C, MeOH, 12 h; (c) 3LiOH, MeOH, 12 h, rt; 1M HCl; (d) 3K$_2$CO$_3$, 1.1 BnBr, MeCN, 12 h, reflux; (e) 70% AcOH, 12-24 h, rt; (f) 1.5 mCPBA, CHCl$_3$, 3-5 h, reflux.

Figure 8:
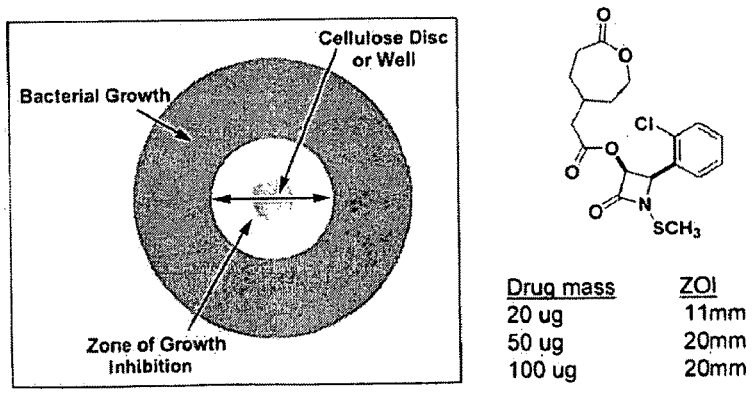
FIG. 8 is an image showing results of biological testing of the lactam-containing monomer vs. MSSA.

Next the functionalized lactone is coupled with an antibiotic, here N-thiolated β-lactam, after deprotection of benzyl ester. FIG. 8 shows the results of biological testing of the lactam-containing monomer vs. MSSA.

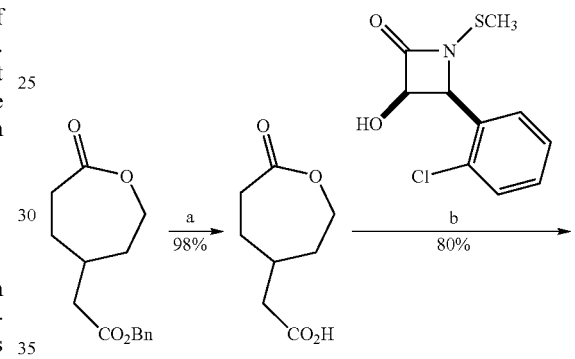

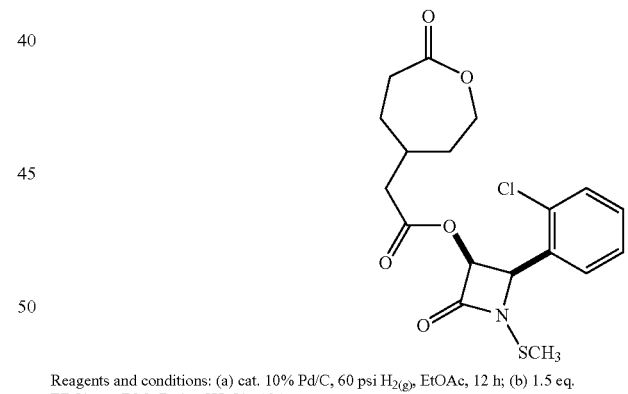

Reagents and conditions: (a) cat. 10% Pd/C, 60 psi H$_{2(g)}$, EtOAc, 12 h; (b) 1.5 eq. EDCl, cat. DMAP, dry CH$_2$Cl$_2$, 12 h, rt.

Example 2

In another embodiment, the invention provides a PCL derived from copolymerization of a functionalized lactone monomer with caprolactone. Copolymers containing 10%, 15%, 20%, 25% and 30% of the substituted lactone were prepared and characterized by TLC, $^1$H, NMR, $^{13}$C NMR and MALDI-TOF. The Copolymers displayed low molecular, between about 1000 and 4000.

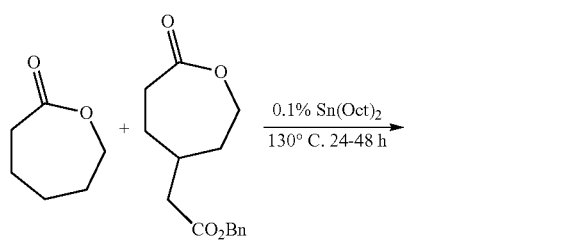

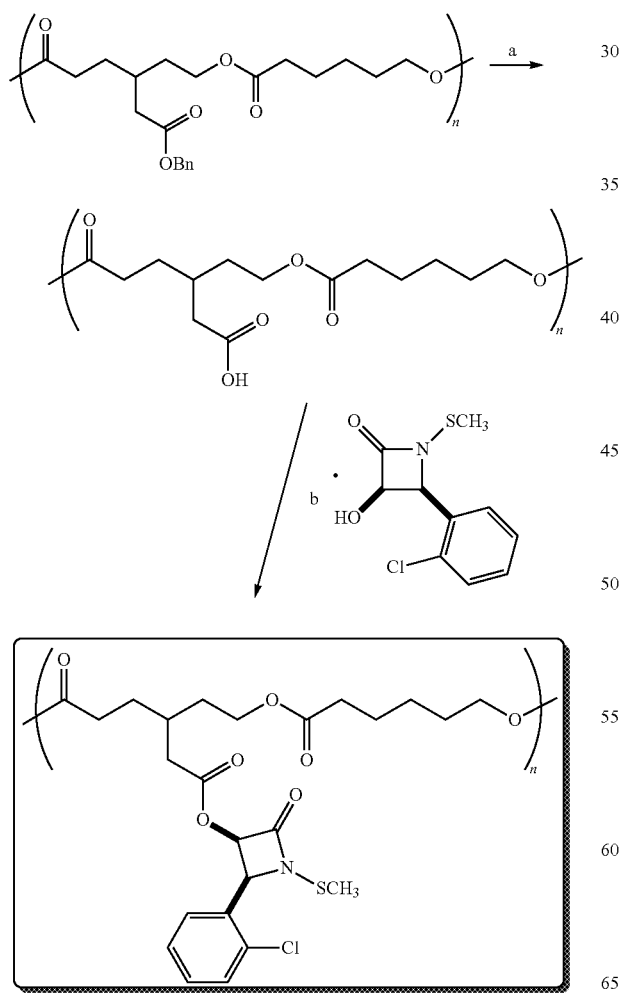

Figure 9:
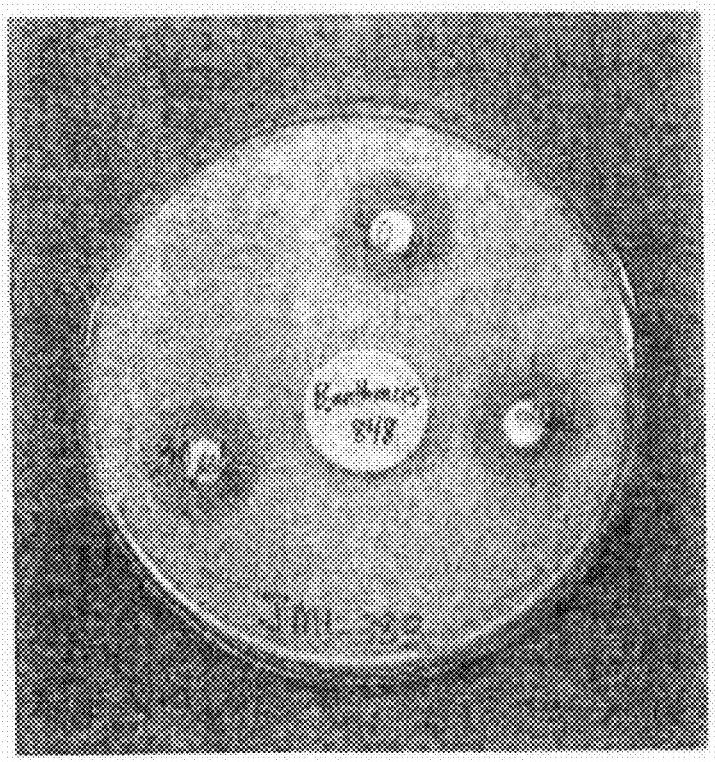
FIG. 9 demonstrates the anti-Bacillus activity of the β-lactam containing copolymer.

Deprotection of the copolymer and coupling with the antibiotic, β-lactam, is shown below and was achieved using the following reagents and conditions: (a) cat. 10% Pd/C, H$_{2(g)}$, EtOAc, 12-24 h. (b) 15 EDCl, cat. DMAP, dry CH$_2$Cl$_2$, 12 h. rt. The antibiotic activity of the completed PCL against *Bacillus* is shown in FIG. 9.

Example 3

Figure 10:
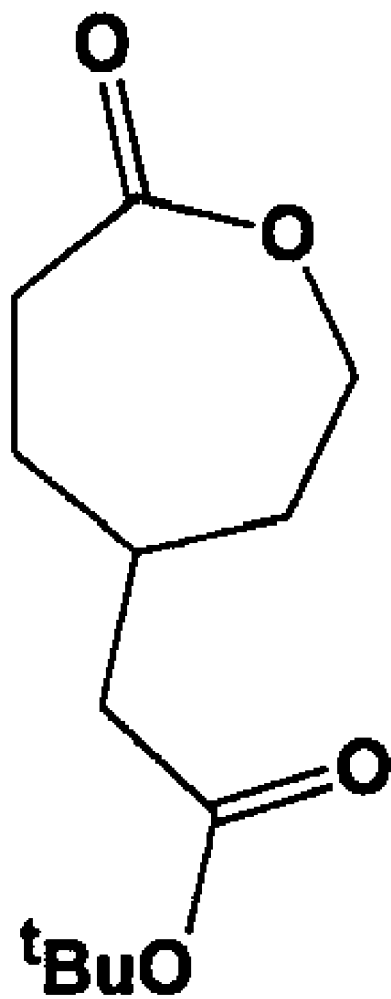
FIG. 10 shows the invention employing an alternate carboxyl protecting group.

In yet another embodiment, the functionalized lactone comprises a carboxy protecting group, as shown in FIG. 10. Ylide synthesis is shown below using the reagents and conditions: (a) PPh$_3$, C$_6$H$_6$, 12 h, rt; (b) 20% NaOH$_{(aq)}$, 5 h, rt.

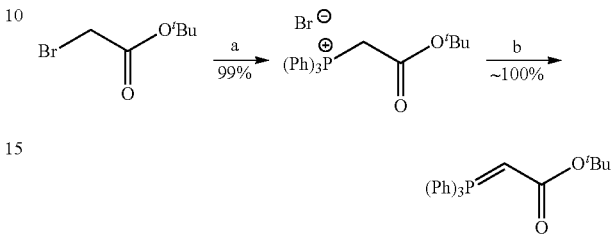

Example 4

The following demonstrates the synthesis of lactone bearing pendant tert-butyl ester using the reagents and conditions: (a) 1.5 eq. ylide C$_6$H$_6$. 12 h, reflux, (b) H$_{2(g)}$, cat. 10% Pd?C, EtOAC, 24 h; (c) 0.1 eq. I$_2$, dry acetone, 1 hr, rt; (d) 1.5mCPBA CHCl$_3$, 3 h, reflux.

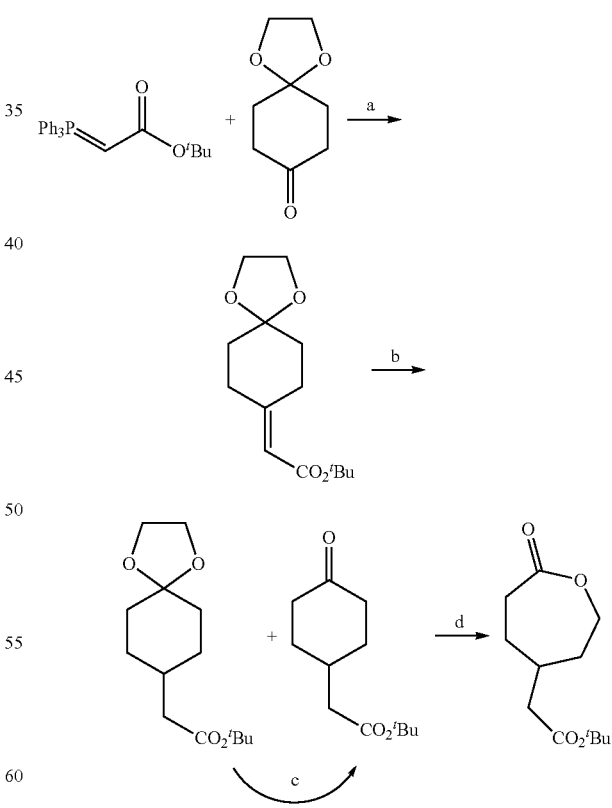

Copolymerization with caprolactone was achieved as shown below. Copolymers containing 10%, and 20% of the substituted lactone were prepared and characterized by TLC, $^1$H NMR and $^{13}$C NMR.

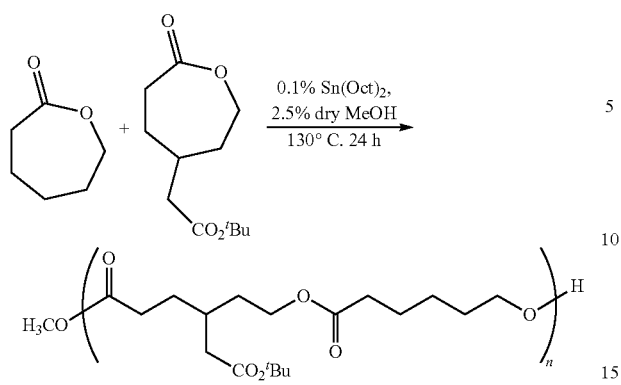

Functional caprolactone monomers have been synthesized and characterized. The monomers were further copolymerized with caprolactone. Caprolactone monomers and polymers with covalently bound N-thiolated β-lactams have been prepared and shown to possess bioactivity against MSSA and *Bacillis* respectively.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A compound consisting of:
   a caprolactone ring;
   a spacer consisting of a methylene group, and a carbonyl group at a terminus of the methylene group, wherein the methylene group at the other terminus is attached to the C-4 position on the caprolactone ring; and
   a 2-azetidinone, wherein an alkylthio is attached to the N-1 position, a hydroxyl group is attached to the C-3 position and an aryl ring is attached to the C-4 position, the C-3 hydroxyl group is joined to the spacer by removing the hydrogen atom of the hydroxyl group.

2. The compound represented by the formula:

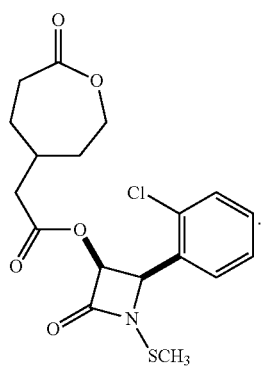

3. The compound represented by the formula:

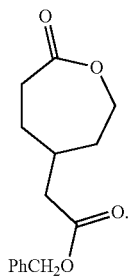

4. The compound represented by the formula:

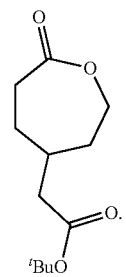

5. A method of producing a compound comprising:
   providing
     a caprolactone ring;
     a spacer, consisting of one methylene group, and a carbonyloxy group at one terminus of the methylene groups, wherein the methylene group at the other terminus is attached to the C-4 position of the caprolactone ring;
     a protecting group, attached to the carbonyloxy group on the spacer;
     a 2-azetidinone, wherein an alkylthio is attached to the N-1 position, a hydroxyl group is attached to the C-3 position and an aryl ring is attached to the C-4 position;
   removing the protecting group from the spacer attached to the caprolactone;
   forming an ester between the hydroxyl group on the 2-azetidinone and the carbonyloxy group on the spacer attached to the caprolactone.

6. The method of claim 5 wherein the protecting group is selected from the group consisting of a benzyl and a tert-butyl.

* * * * *